US008685550B2

(12) United States Patent
Kim et al.

(10) Patent No.: US 8,685,550 B2
(45) Date of Patent: Apr. 1, 2014

(54) BACTERIA/TRANSITION METAL OXIDES ORGANIC-INORGANIC COMPOSITE AND METHOD FOR MANUFACTURING THE SAME

(75) Inventors: Dong-Wan Kim, Seoul (KR); HyunWoo Shim, Daejeon (KR); Young Dae Ko, Seoul (KR); Kyoung Jin Choi, Seoul (KR); Jae-Gwan Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 1175 days.

(21) Appl. No.: 12/462,376

(22) Filed: Aug. 3, 2009

(65) Prior Publication Data

US 2010/0203360 A1     Aug. 12, 2010

(30) Foreign Application Priority Data

Feb. 12, 2009  (KR) .................. 10-2009-0011628

(51) Int. Cl.
 *H01M 8/16* (2006.01)
 *H01M 4/88* (2006.01)
 *B29D 22/00* (2006.01)

(52) U.S. Cl.
 USPC ............ 429/2; 252/182.1; 428/34.1; 977/701

(58) Field of Classification Search
 USPC .............................................. 429/2
 See application file for complete search history.

(56) References Cited

U.S. PATENT DOCUMENTS

| 7,374,893 B2 | 5/2008 | Belcher et al. |
| 2003/0068900 A1 | 4/2003 | Belcher et al. |
| 2006/0014261 A1* | 1/2006 | Phelps et al. .................. 435/168 |
| 2008/0220333 A1 | 9/2008 | Yano et al. |

FOREIGN PATENT DOCUMENTS

JP          03-026680 A       2/1991

(Continued)

OTHER PUBLICATIONS

Dujardin, Erik et al.: "Organization of Metallic Nanoparticles Using Tobacco Mosaic Virus Templates", *Nano Letters*, 2003, vol. 3, No. 3, pp. 413-417.

(Continued)

*Primary Examiner* — Barbara Gilliam
*Assistant Examiner* — Steven Scully
(74) *Attorney, Agent, or Firm* — Frommer Lawrence & Haug LLP; Ronald R. Santucci

(57) ABSTRACT

The present invention relates to an organic-inorganic composite comprising bacteria and transition metal oxides and a method of manufacturing the same. More specifically, the present invention relates to an organic-inorganic composite comprising bacteria and transition metal oxides manufactured by attaching cationic transition metal precursor to bacterial surface, wherein the bacteria with high negative charge on its surface is used as a template, refluxing the bacteria and transition metal ions at room temperature in the presence of sodium borohydride ($NaBH_4$), and inducing reduction/spontaneous oxidation, thereby having an excellent high capacity electrochemical properties, and a method of manufacturing the same.

Therefore, the method of manufacturing the organic-inorganic composite according to the present invention has advantages that it enables to reduce manufacturing cost and the time required therein, mass production, low temperature synthesis, synthesis of uniform nano-structures, control of one dimensional type, be applied to other metal oxides, thus being expected to be used as parts in other electrochemical fields including lithium secondary batteries, super capacitor, nanoelectro-optical system, catalyst and the like.

7 Claims, 13 Drawing Sheets

(56) References Cited

FOREIGN PATENT DOCUMENTS

| JP | 03-063584 | A | 3/1991 |
|---|---|---|---|
| JP | 03-165463 | A | 7/1991 |
| JP | 03-245458 | A | 11/1991 |
| JP | 2006-520317 | A | 9/2006 |
| JP | 2007-517500 | A | 7/2007 |
| JP | 2008-517070 | A | 5/2008 |
| KR | 10-2007-0097028 | A | 10/2007 |
| WO | WO 2004/033488 | | 4/2004 |

OTHER PUBLICATIONS

Yang, Mu et al.: "Synthesis of Spheres with Complex Structures Using Hollow Latex Cages as Templates", *Adv. Funct. Mater.*, 2005, 15, pp. 1523-1528.

Tomczak, Melanie M. et al.: "Polypeptide-Templated Synthesis of Hexagonal Silica Platelets", *J. Am. Chem. Soc.*, 2005, 127, pp. 12577-12582.

Nagamine, Shinsuke et al.: "Preparation of $TiO_2$ hollow microparticles by spraying water droplets into an organic solution of titanium tetraisopropoxide", *Material Letters*, 61 (2007), pp. 444-447.

Joshi, Upendra A. et al.: "Large-Scale, Surfactant-Free, Hydrothermal Synthesis of Lithium Aluminate Nanorods: Optimization of Parameters and Investigation of Growth Mechanism", *Inorg. Chem.*, 2007, 46, pp. 3176-3184.

Chen, Di et al.: "A Simple Aqueous Mineralization Process to Synthesize Tetragonal Molybdate Microcrystallites", *Crystal Growth & Design*, 2006, vol. 6, No. 1, pp. 247-252.

Zhang, Yong et al.: "Fabrication of ZnO hollow nanospheres and "jingle bell" shaped nanospheres", *Material Letters*, 62 (2008) pp. 1435-1437.

Zhou, Han et al.: "Hydrothermal synthesis of ZnO hollow spheres using spherobacterium as biotemplates", *Microporous and Mesoporous Materials*, 100, (2007), pp. 322.327.

Caruso, Frank: "Hollow Inorganic Capsules via Colloid-Templated Layer-by-Layer Electrostatic Assembly", *Top Curr.Chem.*, (2003), 227, pp. 145-168.

Bigall, Nadja C. et al.: "Fungal Templates for Noble-Metal Nanoparticles and Their Application in Catalysis", *Angew. Chem. Int. Ed.*, 2008, 47, pp. 7876-7879.

Nomura, T. et al.: "Fabrication of silica hollow particles using *Escherichia coli* as a template", *Material Letters*, 62 (2008) pp. 3727-3729.

Darn, J.R. et al.: "The "Falling Cards Model" for the Structure of Microporous Carbons", *Carbon*, vol. 35, No. 6, 1997, pp. 825-830.

Alcantara, R. et al.: "Negative Electrodes for Lithium- and Sodium-Ion Batteries Obtained by Heat-Treatment of Petroleum Cokes below 1000° C.", *Journal of The Electrochemical Society*, 149, (2), 2002, pp. A201-A205.

Shaju, Kuthanapillil M. et al.: "Mesoporous and nanowire $CO_3O_4$ as negative electrodes for rechargeable lithium batteries", *Phys. Chem. Phys.*, 2007, 9, pp. 1837-1842.

Chan, Candace K. et al.: "High Capacity Li Ion Battery Anodes Using Ge Nanowires", *Nano Letters*, 2008, vol. 8, No. 1, pp. 307-309.

Chan, Candace K. et al.: "High-performance lithium battery anodes using silicon nanowires", *nature nanotechnology*, vol. 3, Jan. 2008, pp. 31-35.

Yang, Ruizhi et al.: "Nano $CO_3O_4$ Particles Embedded in Porous Hard Carbon Spherules as Anode Material for Li-Ion Batteries", *Electrochemical and Solid-State Letters*, 7 (12), 2004, pp. A496-A499.

Poizot, P. et al.: "Nano-sized transition-metal oxides as negative-electrode materials for lithium-ion batteries", *Nature*, vol. 407, Sep. 28, 2000, pp. 496-499.

Weydanz, W .J. et al.: "A room temperature study of the binary lithium-silicon and the ternary lithium-chromium-silicon system for use in rechargeable lithium batteries", *Journal of Power Sources*, 81-82, (1999), pp. 237-242.

T. Herrmannsdöerfer, et al., "Magnetic properties of transition-metal nanoclusters on a biological substrate," Journal of Magnetism and Magnetic Materials, 310 (2007), pp. e821-e823.

Xin Liang, et al., "Magnetic and mechanical properties of micro/nano particles prepared by metalizing rod-shaped bacteria," Materials Letters, 62 (2008), pp. 2999-3002.

V. Berry, et al., "Highly Selective, Electrically Conductive Monolayer of Nanoparticles on Live Bacteria," 2004, vol. 4, No. 5, pp. 939-942.

* cited by examiner

BACTERIA/TRANSITION METAL OXIDES ORGANIC-INORGANIC COMPOSITE AND METHOD FOR MANUFACTURING THE SAME

CROSS-REFERENCE TO RELATED APPLICATION

This application claims the benefit under 35 U.S.C. §119 (a) of Korean Patent Application No. 10-2009-0011628 filed on Feb. 12, 2009, the entire contents of which are incorporated herein by reference.

BACKGROUND (a) Technical Field

The present invention relates to an organic-inorganic composite comprising bacteria and a transition metal oxide organic-inorganic composite.

(b) Background Art

For the last two decades, microsystem and nanotechnology have been developed rapidly having a wide spectrum of its applications in various fields of industry including automobile parts, electronic products, medical devices, thereby requiring light-weightness, compactness, high integration of the above products. Further, with the introduction of full-fledged era of nanotechonology, research has been conducted on nano-structured materials at a nanoscale level such as nanowire, nanobelt, nanorod, quantum dot, even advancing to nano robots to be used for the treatment of human diseases.

In fact, many researches have been focused on the synthesis of nano-structured inorganic materials because nano-structured inorganic materials exhibit unique characteristics, which have not been observed in micro-sized materials, and also revealed various excellent properties including more improved electromagnetic and optical properties, catalytic functions and high specific surface area than those with large capacity, thus being applicable to various fields. However, the conventional nano-structured inorganic materials, although synthesized using various materials and methods, have been highly limited in their forms produced [D. Chen et al., Cryst. Growth Des. 6 (2006) 247; U. A. Joshi et al., Inorg. Chem. 46 (2007) 3176; S. Nagamine et al., Mater. Lett. 61 (2007) 444].

Of methods attempted in synthesizing various forms of nano-structured inorganic materials, the method using a template is a representative method which enables to easily obtain various kinds of particular forms of nano-structured materials depending on the type of the template to be used. In particular, unique forms of nano-structured materials can be obtained by using various materials and structures including DNA molecules containing essential nucleotides for genes, polystyrene beads, anodizing aluminum oxides (AAO) [M. M. Tomczak et al., J. Am. Chem. Soc. 127 (2005) 12577; M. Yang et al., Adv. Funct. Mater. 15 (2005) 1523]. Further, there have been a few reports with the increase in synthesis of nano-structured inorganic materials using biomaterials such as proteins, viruses, bacteria, yeast, and fungi as templates [E. Dujardin et al., Nano Lett. 3 (2003) 413; T. Nomura et al., Mater. Lett. 62 (2008) 3727; N. C. Bigall et al., Angew. Chem. Int. Edit. 47 (2008) 7876; U.S. Patent Publication Nos. US20030068900; US20070287174; Japanese Patent Publication Nos. 2006-520317; 2007-517500]. Although the above method enables to obtain various forms of nano-structured inorganic materials by using various templates it also has drawbacks requiring a complex intermediate process such as surface treatment or addition and removal of a surfactant and also conducting the synthesis at high temperature to obtain inorganic materials with high crystallinity [F. Caruso, Top. Curr. Chem. 227 (2003) 145; H. Zhou et al., Microporous Mesoporous Mat. 100 (2007) 322; Y. Zhang et al., Mater. Lett. 62 (2008) 1435]. Especially, in case the biomaterials such as proteins, viruses, and bacteria are used as templates they may be broken or removed before the synthesis of inorganic materials thus not being able to obtain the materials with desired forms. Therefore, when synthesizing nano-structured inorganic materials using the above as templates it is necessary to provide a simplified process of synthesis as well as low temperature synthesis.

As mentioned above, nano-structured inorganic materials exhibit superior properties in many fields to be applicable to a variety of fields including nanoelectronics, photonics, catalysts, sensors, and energy storage. Therefore, in the present invention, nano-structured inorganic materials were manufactured using the above-mentioned template method; in particular, rod-shaped transition metal oxides and tube-shaped transition metal oxides were manufactured by using *Bacillus* bacteria with high electric potential as a template.

Notably, the problem of the method of the conventional synthesis with a complex process performed at high temperature (90-600° C.) is resolved in the present invention by attaching transition metal cations to negatively charged bacterial surface via electrostatic force without special surface treatment of the template, and performing reduction/spontaneous oxidation of the transition metal ions attached to the surface at room temperature by using a reducing agent. Further, not only rod-shaped but also tube-shaped one dimensional rods can be obtained by removing only the bacteria, which was used as a template, via calcination of rod-shaped nano-structured inorganic materials produced thereof. The nano-structured materials manufactured thereof can be applied to the manufacture of lithium ion secondary battery electrodes.

The above is due to the recent trend of achieving light-weightness, compactness, high density, and high integration in the field of portable electronic products such as laptop computers, mobile phones, and musical instruments. Further, with the recent growing concerns on safe environment, researches on the development of environment-friendly products such as electrical vehicles and hybrid vehicles have been performed actively thus requiring the development of technologies related to high capacity system and high power system of batteries used as electric sources for their locomotion.

Recently, various research developments using biomaterials as template and their applications in lithium secondary batteries have been reported [Published Korean Patent Application No. 2007-0097028; Published U.S. Patent Application No. US20080220333; Published Japanese Patent Application No. 2008-517070].

Unlike the primary batteries, which allow only a single use, secondary batteries in general are reusable by recharging. The primary batteries such as alkali batteries, mercury batteries, and manganese batteries with relatively high capacity, which are more commonly used, are not reusable and also not environment-friendly. Meanwhile, the secondary batteries such as lead storage batteries, nickel-cadmium batteries, nickel metal hydride batteries, lithium metal batteries, and lithium ion batteries are reusable, more energy-efficient than the primary batteries due to high voltage, environment-friendliness, while having high capacity and high energy density unlike the fuel cells, which have technical limitations due to their low energy density, thus being commercialized in various industrial fields.

Of these, the lithium ion batteries utilize the reversible insertion/deinsertion reaction occurring when lithium ions present in electrolytes, being lithium ionic conductor, move to either an anode active material or a cathode active material, where a lithium metal was first used as the anode active material. However, the research on this field has not been pursued further because of the drastic decrease in charge/discharge capacity due to the change in the shape of the electrode surface and the risk of explosion occurring in case there is a contact between the lithium metal dendrites generated from the negative electrode and the positive electrode.

In 1991, since SONY first used carbon as an anode active material and a lithium cobalt oxide as a cathode active material the term 'lithium ion secondary battery' has been used, and until now, anode active material based on reversible insertion/deinsertion reaction of carbon materials serves as a core part of the lithium ion secondary battery technology.

Of these, carbons such as hard carbons (nongraphitizable carbons), soft carbons and graphites are most widely used. Non-graphitic carbons such as hard carbons and soft carbons are not only capable of intercalating between layers in a layered structure but also capable of storing lithium ions via pores present inside carbons thus providing a much larger capacity than those of graphitic carbons, however, they have a drawback that they have a high irreversible capacity [R. Alcantara et al., J. Electrochem. Soc. 149 (2002) A201; J. R. Dahin et al., Carbon 35 (1997) 825-830].

Of carbon materials, graphite has been most widely commercialized. However, it also has drawbacks of having high cost, low capacity due to complex process, and difficulty in manufacturing high density electrodes in a planar form as is the case with natural graphite. Therefore, there was developed a new method of doping an atom such as boron to low price cokes-based artificial graphite and using thus prepared doped graphite as an anode active material [Japanese Patent Publication Hei 3-165463; Hei 3-245458; Hei 5-26680; Hei 9-63584].

However, the above carbon-based anode active material in general has a less theoretical capacity (372 mAh/g) and the commercialized capacity is known to be even less than the above. Further, it is not sufficient to meet the high capacity system required in portable electronic devices or electric vehicles because of the increase in the irreversibility of lithium secondary batteries caused by a subreaction occurring between an anode active material and an electrolyte solution during the charge/discharge process.

Accordingly, active researches have been performed on the anode active materials to replace the carbon-based materials, for example, transition metal oxides such as CuO, CoO, $Fe_2O_3$, NiO, and $MnO_2$ which exhibit high capacity by alloying reactions to synthesize alloys with lithium such as Si, Ge, and Sn or conversion reaction between metals, instead of the conventional insertion/deinsertion process [W. J. Weydanz et al., J. Power Sources 237 81 (1999) 237-242; P. Poizot et al., Nature 407 (2000) 496].

Of these, in lithium secondary batteries, which are proceeded by the conversion reaction between metals, metal oxides undergo the charge/discharge process by a conversion reaction such as $M_xO_y + 2yLi \leftrightarrows xM + yLi_2O$ (M=transition metal), and also $Li_2O$, which has long been considered not having electrochemical activity, expresses capacity while reacting irreversibly, therefore having an advantage of higher charge/discharge capacity than the insertion/deinsertion process. However, it has a drawback that the capacity rapidly decreases according to the increase in the number of cycles due to the aggregation among particles during the charge/discharge process. [R. Yang et al., Electrochem. Solid-State Lett. 7 (2004) A496-A499].

As a way to solve the above problem, there has been an attempt to use a low dimensional structure, in particular one dimension nanostructure such as nanowires, as an anode active material. However, this also has disadvantages that its manufacturing process is very complex and also a mass production is not possible [C. K. Chan et al., Nature Nanotech. 3 (2008) 31; C. K. Chan et al., Nano Lett. 8(1) (2008) 307; K. M. Shaju et al., Phys. Chem. Chem. Phys. 9 (2007) 1837].

From the above, it is apparent that there is a need for the development of a novel anode active material which has high capacity and enables to stably retain its high capacity during a long term charge/discharge process to replace the conventional carbon-based materials.

SUMMARY OF THE DISCLOSURE

The present invention has been made to solve the foregoing problems of the prior art. The inventors of the present invention discovered that when one dimensional organic/inorganic composite consisting of zero dimension obtained by uniform binding of transition metal oxides on the bacterial surface; or rod-type transition metal oxide powder obtained by removing only the bacterial template, where both of which were prepared by using bacteria having negative charge on the surface as a template, is used as an anode active material, high capacity electrochemical properties were obtainable because one dimensional metal oxides consist of zero dimensional metal oxides (nanoparticles), due to their higher specific surface area than those of one dimensional metal oxides, and by uniformly attaching metal cations to the bacteria surface by electrostatic force, and concurrently performing reduction/spontaneous oxidation of the attached transition metal ions at room temperature by using a reducing agent.

Therefore, an object of the present invention is to provide a method of manufacturing one dimensional organic-inorganic composite or a tube-shaped rod comprised of nanostructures of zero dimension, in the course of manufacturing metal oxide nanopowder, by binding transition metal oxides to bacterial surface by using bacterial template. The above method is a very simple process and can be performed at room temperature (20-30° C.). Moreover, it is possible to produce massively due to the easy mass production of bacterial cultivation.

Another object of the present invention is to provide an organic-inorganic composite comprising bacteria and transition metal oxides by the redox of bacteria with negative charge and cations of transition metal ions.

A further object of the present invention is to provide a method for manufacturing the organic-inorganic composite comprising bacteria and transition metal oxides by the redox of bacteria with negative charge and cations of transition metal ions.

A still further object of the present invention is to provide a method for manufacturing the organic-inorganic composite comprising bacteria and transition metal oxides by the redox of bacteria with negative charge and cations of transition metal ions in the form of a rod and a tube.

A yet still further object of the present invention is the use of the organic-inorganic composite comprising bacteria and transition metal oxides by the redox of bacteria with negative charge and cations of transition metal ions.

The present invention relates to a method of manufacturing an organic/inorganic composite comprising bacteria and a transition metal oxide comprising the steps of:

(a) preparing a culture of bacteria with negative surface charge, adjusting the concentration of the cultured bacteria using deionized water, and preparing a bacteria suspension therefrom;

(b) adding a transition metal precursor solution, wherein a transition metal precursor is dissolved in deionized water, to the solution obtained in the above step (a) while stirring at 20-30° C. for 0.5-2 hours, thereby uniformly dispersing said bacteria and the transition metal precursor;

(c) refluxing a transition metal precursor solution, wherein sodium borohydride ($NaBH_4$) is dissolved in deionized water, while adding it to the solution obtained in the above step (b), thereby allowing the transition metal oxide to be uniformly attached on the bacterial surface;

(d) centrifuging the refluxed solution followed by washing to obtain a deposit; and (e) drying the deposit under vacuum to obtain an organic/inorganic composite.

Further, the present invention relates to a method for manufacturing the above organic-inorganic composite in the form of a tube-shaped rod by performing calcinations at atmospheric pressure.

Further, the present invention relates to the tube-shaped transition metal oxides rod prepared by using the above method.

Further, the present invention relates to an anode active material for manufacturing secondary batteries comprising the above organic-inorganic composite or tube-shaped transition metal oxides rod.

Further, the present invention relates to a secondary battery comprising an anode which includes the above anode active material.

Advantageous Effects

*Bacillus* bacteria/transition metal oxides organic-inorganic composite of the present invention, manufactured by directly attaching cations of transition metal precursor on the surface of bacteria with negative charge followed by reflux, can be prepared in the form of a rod or tube of one dimension by using transition metal oxides of zero dimension.

The above method is a simple process which enables a mass production by using bacteria, which can be also prepared in large scale, as a template, via electrostatic force due to opposite charges, thus being economical in terms of cost and time.

Further, *Bacillus* bacteria used as a template can be present in the form of a rod, circle or oval, it can be used to manufacture various one dimensional forms of organic-inorganic composites.

Further, in electrochemical aspect, it enables to retain high capacity because of transition metal oxides and high output without much change in volume in reacting with lithium during a long term use.

Further, the organic-inorganic composite of the present invention has a relatively large specific area because transition metal oxides nanopowder consist of zero dimensional nanostructure materials, which are uniformly distributed over the bacterial surface by which one dimensional shape is established.

Therefore, the organic-inorganic composite of the present invention using bacteria with negative charge on its surface as a mediator is easily synthesized, is economical, and enables a mass production, thus being expected to be used in various fields of industry including lithium secondary batteries, electric double layer super capacitor (ELSC), pseudo super capacitor (PSC), etc.

BRIEF DESCRIPTION OF THE DRAWINGS

The above and other features of the present invention will now be described in detail with reference to certain exemplary embodiments thereof illustrated the accompanying drawings which are given herein below by way of illustration only, and thus are not limitative of the present invention, and wherein.

DETAILED DESCRIPTION OF THE INVENTION

Figure 1:
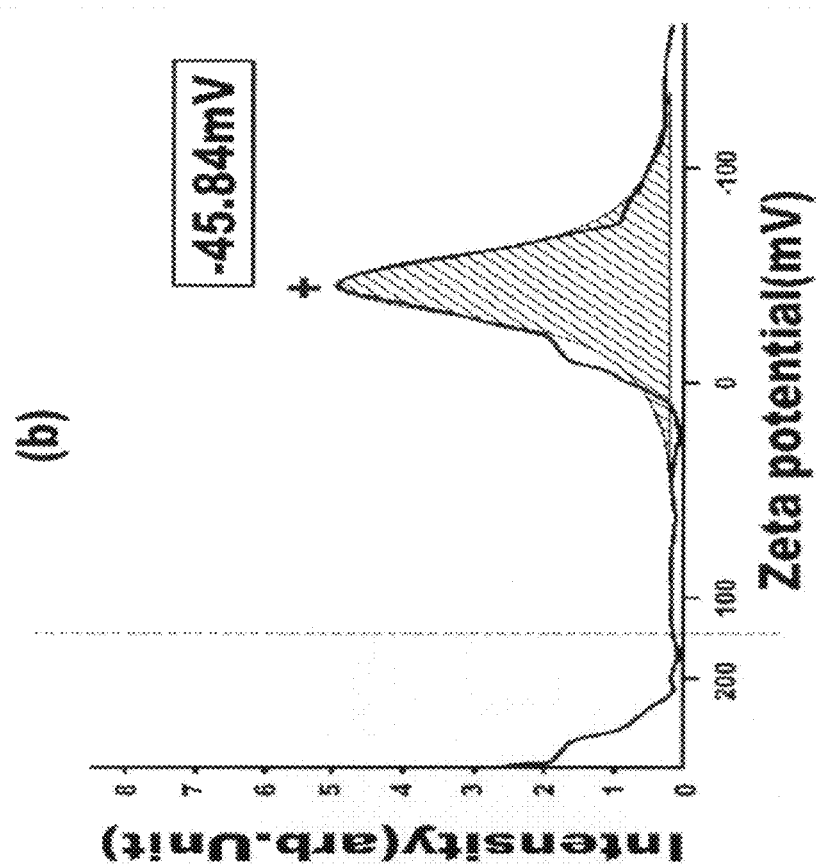
FIG. 1(*a*) shows a of pure *Bacillus* bacteria taken under Field Emission Scanning Electron Microscopy (FESEM) and FIG. 1(*b*) shows a graph of the negative electric potential on *Bacillus* bacterial surface measured by means of zeta potential.
Figure 1:
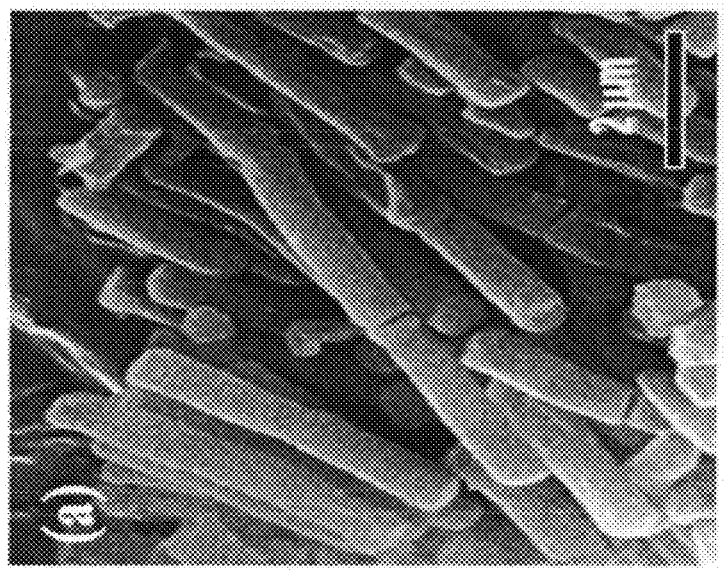

The present invention is described in further detail as set forth hereunder.

The present invention relates to a bacteria-transition metal oxides organic-inorganic composite, and a tube-shaped transition metal oxides rod of one dimension comprising nanopowder of zero dimension exhibiting high capacity as well as effective stress relieving effect through uniform and even distribution of transition metal oxides on bacterial surface by directly attaching transition metal precursor to the bacterial surface via electrostatic force between transition metal precursor and bacterial surface and performing reduction/spontaneous oxidation of transition metal precursor by using a reducing agent, based on the discovery that transition metal precursors take on cationic properties in a solution and by using rod-shaped *Bacillus* bacteria with high negative charge on the surface, and method of manufacturing the same.

There is no limitation with regard to a transition metal to be used in the present invention, however, the fourth period metals in the periodic table, for example, Cu, Co, Fe, Ni, Mn, Ti, etc., are preferred. Examples of the transition metal precursors include nitrates, chlorides, acetates, etc.

In the organic-inorganic composite using bacteria as a template suggested in the present invention, the transition metal oxides bound to bacterial surface can be synthesized by using a solution-based synthesis method where the cations of transition metal ions attached to the bacterial surface by means of electrostatic force are reduced by using sodium borohydride ($NaBH_4$), a reducing agent, while concurrently conducting an oxidative process.

The methods of synthesizing metal oxide powder include vapor-phase reaction, solid-phase reaction, and liquid-phase reaction. The gas-state reaction method has an advantage that it produces powder with high crystallinity but has a drawback that it is a complex process. The solid-state reaction method has an advantage that it is economical but has disadvantages that uniform powder is hardly obtained by the method and also the particles produced are large in size. On the other hand, the liquid-state reaction method, although it does not produce powder with high crystallinity, has advantages that it enables to obtain crystalline materials at low temperature depending on the synthetic conditions and also that it produces uniform powder with small size.

Further, the process of synthesizing organic-inorganic composite of the present invention by using bacteria with negative surface charge as a template has advantages that it is a simple process, enables to obtain powder with uniform size and crystallinity at room temperature (20-30° C.), and also enables a mass production.

Further, with regard to the use of the template bacteria, it is possible to use bacterial strains of various forms thus making it possible to obtain various kinds of one dimensional organic-inorganic composites and their modifications which have been hardly achieved by using the conventional methods.

The shape of the *Bacillus* bacteria used as a template for the manufacture of bacteria/transition metal oxides organic-inorganic composite in the present invention can be observed under Field Emission Scanning Electron Microscopy (FESEM), and the characteristics of the negative charge exhibited on the surface can be confirmed by measuring Zeta potential (FIG. 1). According to FIG. 1, the *Bacillus* bacteria used as a template has a rod shape, and shows the properties of negative electric potential having a relatively high Zeta potential of −45.84 mV.

Figure 2:
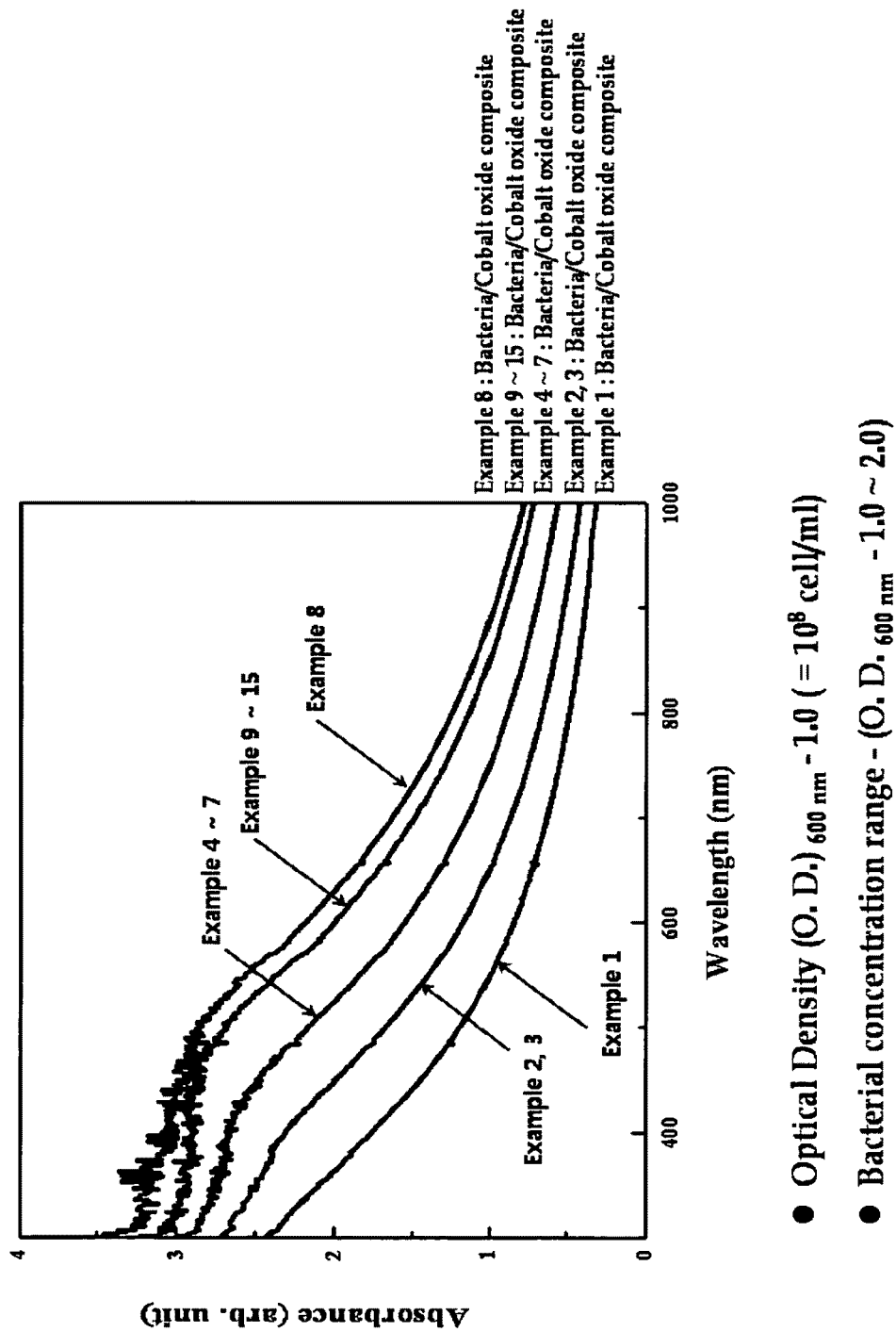
FIG. 2 shows the result of optical density representing the range of concentration of *Bacillus* bacteria used as a template in the present invention, wherein optical density at 600 nm is about 1.0, which indicates that the bacterial density is about $10^8$ cells/mL)

Further, the concentration of the bacterial template used for the manufacture of the above organic-inorganic composite can be confirmed by measuring optical density at 600 nm using a UV spectrometer (FIG. 2).

As shown in FIG. 2, the concentration of the bacterial template is preferably in the optical density range of 1.0-2.0 at 600 nm.

The concentration of the bacterial template is adjusted as follows.

First, a sample of the initial bacterial culture is collected, subsequently subcultured in an Erlenmeyer flask containing a liquid culture medium, the bacterial culture is separated from the supernatant by centrifugation, the bacterial cluster at the bottom of a tube is washed with deionized water and centrifuged. Then, a sample is collected from the diluted bacterial suspension while adding deionized water thereto and its optical density is measured at 600 nm. The addition of deionized water and subsequent measurement of the bacterial culture sample using a UV spectrometer is repeated until the bacterial culture concentration reaches an appropriate level.

Figure 3:
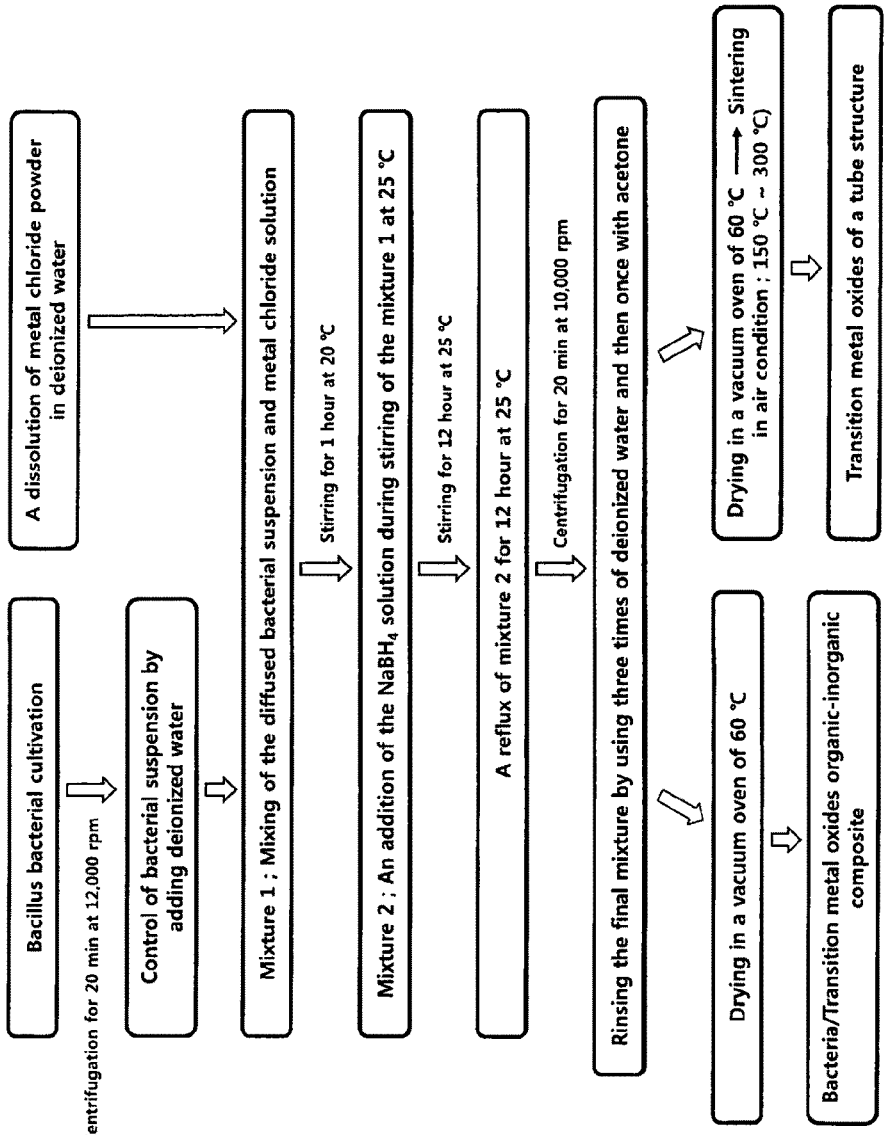
FIG. 3 shows a flow chart for the manufacturing process of organic-inorganic composite comprising organic bacteria and inorganic transition metal oxides.

The method of synthesizing one dimensional organic-inorganic composite consisting of zero dimension and anode active material in the form of a tube-shaped rod are shown in FIG. 3, and its details are explained below with reference to FIG. 3.

First, for the preparation of bacteria to be used as a template, a sample of a bacterial stock solution, which has been kept frozen, is collected, is subsequently subjected to initial cultivation, and then subcultured in an Erlenmeyer flask where initial bacterial culture of 10-12 hours and a liquid culture medium are contained. Then, the resultant is subject to centrifugation and washing, and its concentration is adjusted by adding deionized water at room temperature while stirring. In collecting bacteria after the above centrifugation, if the centrifugation is conducted for less than five hours from the start point of the subculture the amount of bacteria decreases and thus the amount of the deposit to be obtained eventually will also decrease. Therefore, it is preferable to perform the above centrifugation using a bacterial subculture of 5 hours or longer, when the bacterial growth reaches the end portion of its growth curve.

While the dispersed bacterial suspension adjusted to an appropriate concentration is maintained while stirring, a transition metal precursor is added into deionized water to prepare a metal chloride precursor in the range of 1-100 mM, and dissolve the metal chloride precursor to be fully dispersed while stirring. Then, the dissolved transition metal precursor solution is slowly added to a bacteria dispersed solution while stirring. Here, if the transition metal precursor solution is rapidly added the transition metal precursor may not be evenly attached to the surface of dispersed bacteria, and also it may be difficult to obtain a suitable single rod-shape due to the aggregation among bacteria and partial reflux during the subsequent process of reduction by a reducing agent of sodium borohydride and the spontaneous oxidation in an aqueous solution. Therefore, it is preferable that the transition metal precursor is added slowly using a burette. Then, for the sufficient attachment between cations of the transition metal precursor and the bacterial surface and the uniform distribution and dispersion of the transition metal precursor thereon, sufficient stirring at 20-30° C. for 0.5-2 hours is maintained. In particular, the attachment of cations of the transition metal precursor to the surface of *Bacillus* bacteria is due to the highly negative charge of the bacterial surface. In fact, the high negative charge on the surface of the *Bacillus* bacteria is due to the presence of functional groups such as phosphoric group ($PO_3^{2-}$) and carboxyl group (COO—) in polymer chains such as peptidoglycan layer, teichoic acid, and teichuronic acid which constitute the bacterial cell membrane. In particular, *Bacillus* bacteria is a gram positive bacteria, and, unlike the gram negative bacteria such as *E. coli*, has a thicker peptidoglycan layer and has no outer membrane and thus peptidoglycan layer and polymer chains are directly exposed to external environment thereby having a higher negative charge. In case of *E. coli* (−28.69 mV) and *Pseudomonas* (−18.76 mV), which belong to gram negative bacteria, they have a weaker negative charge on the surface than the *Bacillus* bacteria, a gram positive bacteria, but they can be used as a template in the present invention. Therefore, any bacteria which has negative charge on its surface may be used as a template in the present invention, and preferably a gram negative bacteria or gram positive bacteria.

While the mixture of the above bacterial template and the transition metal precursor are being stirred for 0.5-2 hours at 20-30° C., sodium borohydride is added to deionized water to prepare sodium borohydride solution, and is dissolved for sufficient dispersion while stirring. Then, the dissolved sodium borohydride solution is slowly added to a mixture of bacterial template and transition metal precursor while stirring. Here, the above solution is added slowly using a burette, as is the case with the above-mentioned addition of the transition metal precursor, at a rate of 0.5-3 ml/min.

If the sodium borohydride solution, which serves as a reducing agent, is added rapidly it will result in a rapid redox reaction. This will cause the solution not to react with the entire precursors of cations attached to the bacterial surface but only in a limited area, thus not enabling to achieve uniform distribution of metal oxides over the bacterial surface, and also due to partial reflux, the bacterial aggregation and a suitable single rod-shaped form will be difficult to obtain.

Then, it is necessary to continue to stir the solution so that sodium borohydride is dispersed evenly in the solution and thus the metal precursors of cations attached to the bacterial surface can be uniformly distributed to metal oxides.

The above mixture containing sodium borohydride as a reducing agent is refluxed for 10-15 hours while stirring at 20° C.-30° C., and centrifuged. The supernatant is discarded and the precipitate in the bottom is collected and washed with deionized water and acetone. The deposited precipitate is evenly distributed and attached to *Bacillus* bacterial surface, and is disclosed in various colors of pink, black, yellowish green, emerald, etc., depending on the synthetic conditions, which are shown in examples.

Then, a drying process is conducted in a vacuum oven. The dry under vacuum of the present invention is conducted at 60-70° C. under $10^{-2}$-$10^{-3}$ torr for 6-8 hours. The final powder of organic-inorganic composite obtained as a result of the above vacuum dry has such a shape that the bacterial surface with 500-800 nm of diameter and 1-2 μm of length is evenly surrounded with transition metal oxides nanopowder of 2-5 nm in size, and the oxide nanopowder has a highly homogeneous and fine size distribution.

Figure 4:
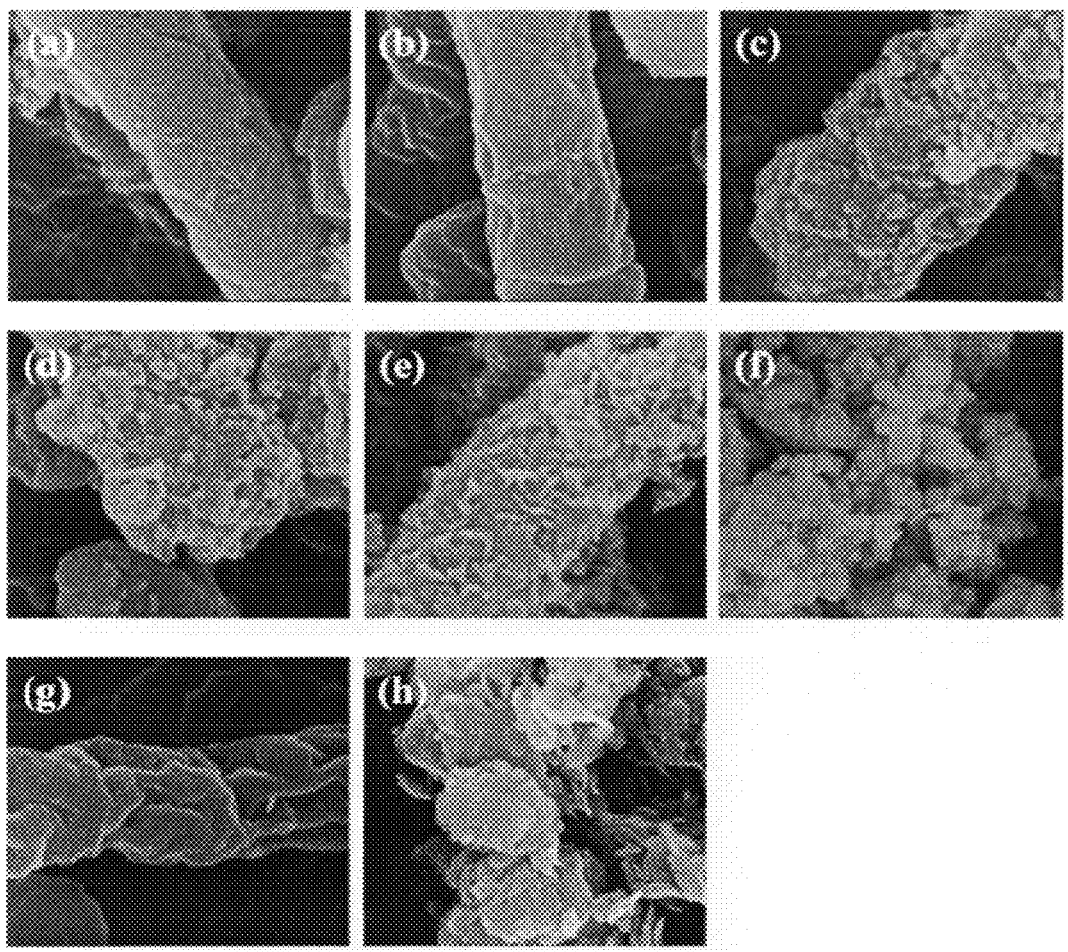
FIG. 4 shows the pictures of shapes of *Bacillus* bacteria/transition metal oxides organic-inorganic composite and the pure transition metal oxides without using bacteria both taken under FESEM [(a)-(f) *Bacillus* bacteria/cobalt. oxide, (g) *Bacillus* bacteria/iron oxide, (h) cobalt oxide not using bacteria as a template]

The shape of thus obtained bacteria/transition metal oxides organic-inorganic composite can be observed via FESEM pictures (FIG. 4), wherein various surface types are disclosed depending on the conditions of synthesis.

Figure 5:
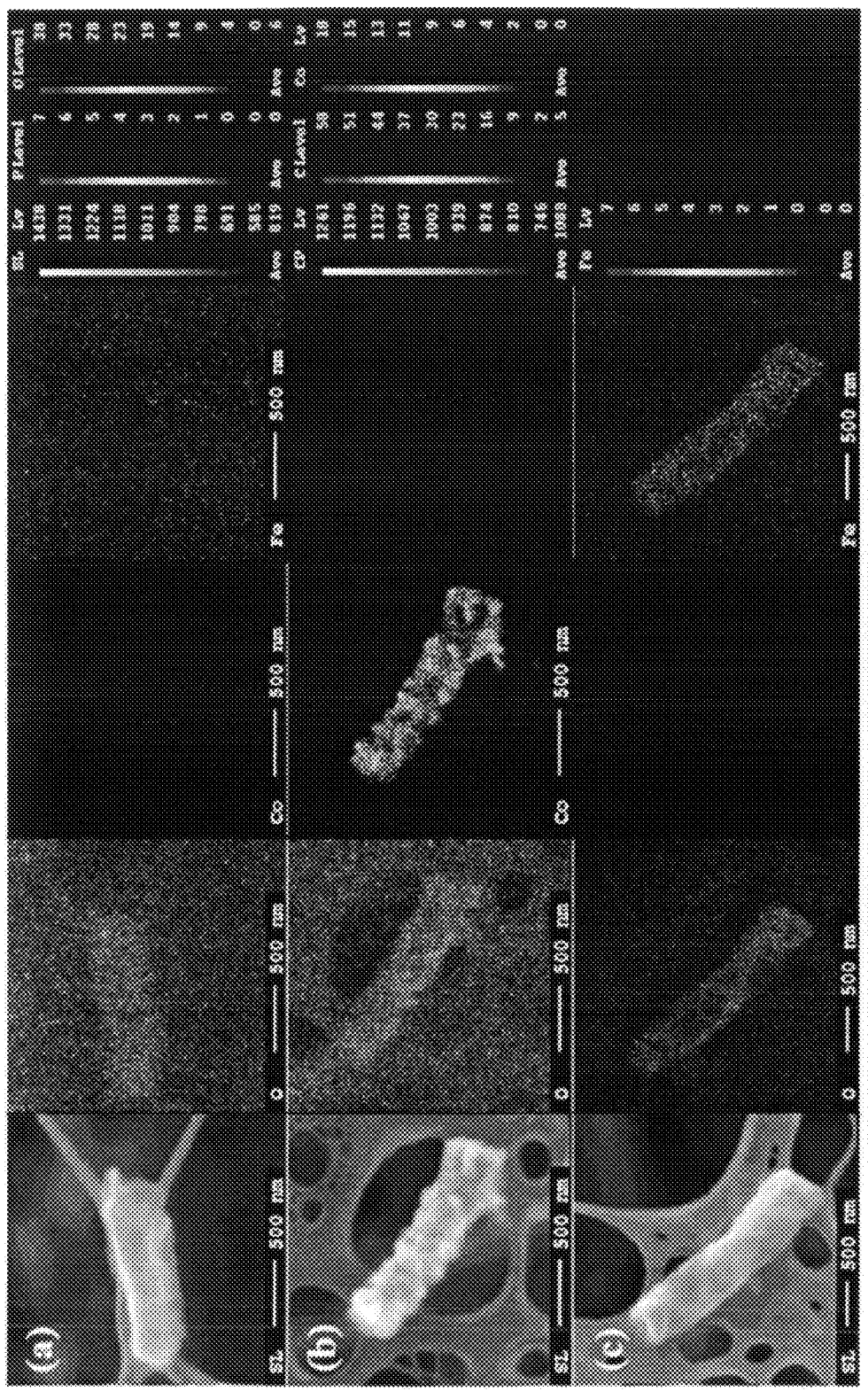
FIG. 5 shows the pictures of exact synthesis of *Bacillus* bacteria/transition metal oxides organic-inorganic composite, via analyses of cobalt, iron, oxygen atoms, manufactured according to the present invention taken under Electron Probe Microanalyzer (EPMA) [(a) pure *Bacillus* bacteria, (b) *Bacillus* bacteria/cobalt oxide, (c) *Bacillus* bacteria/iron oxide]
Figure 6:
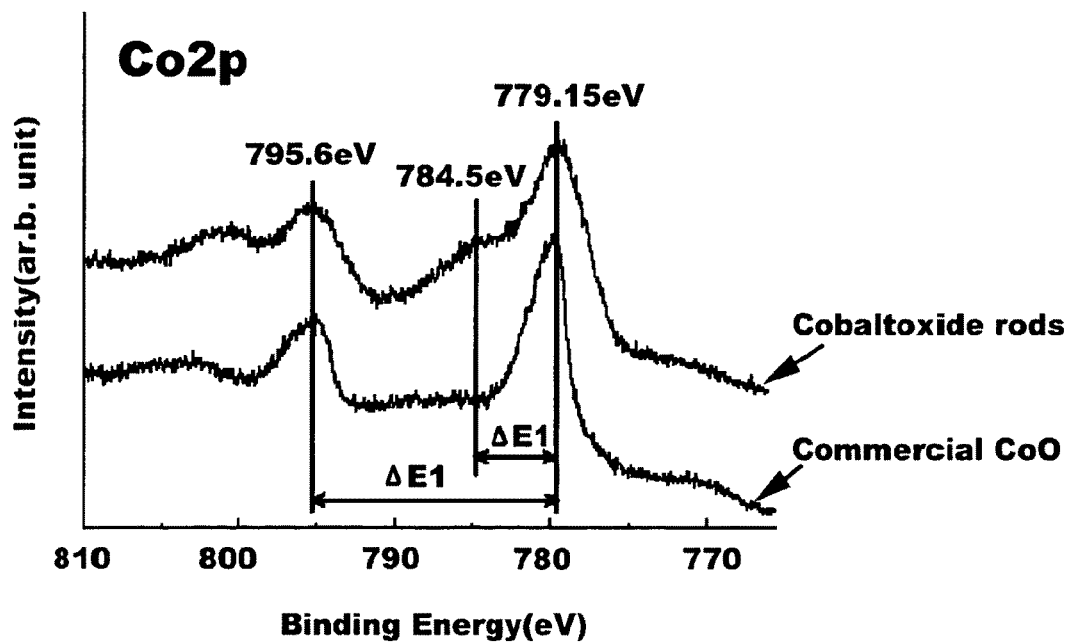
FIG. 6 shows the result of analysis of cobalt oxide attached to *Bacillus* bacterial surface by using X-ray Photoelectron Spectroscopy (XPS)
Figure 7:
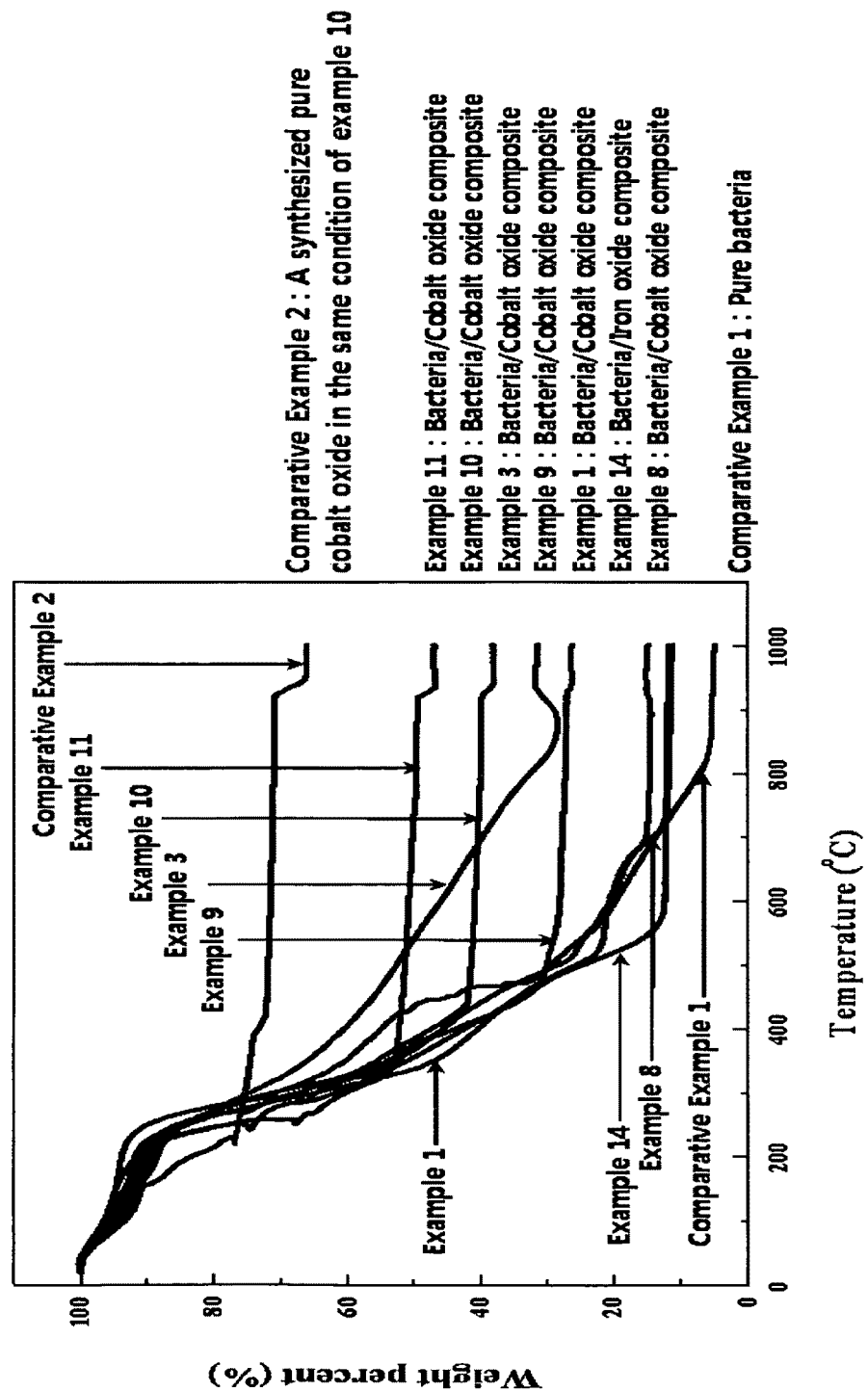
FIG. 7 shows the result of analyses of *Bacillus* bacteria/transition metal oxides organic-inorganic composite manufactured in the present invention, pure transition metal oxides without using bacteria, and pure organic bacteria by using Thermogravimetry Analyzer (TGA)

Further, the result of synthesis of the bacteria/transition metal oxides organic-inorganic composite can be confirmed by means of Electron Probe Microanalyzer (EPMA) of transition metal atoms and oxygen (FIG. 5) and X-ray Photoelectron Spectroscopy (XPS) (FIG. 6). In addition, FIG. 7 reveals the quantitative comparison of transition metal oxides attached according to the synthetic conditions by using Thermogravimetry Analyzer (TGA).

Part of the precipitates, which has undergone up until the stage of the vacuum dry for the manufacture of a tube from a rod, is calcined under air atmosphere. The above air atmosphere combustion is performed in such a manner that temperature is increased to 150-300° C. at a rate of 1-10° C./min under air atmosphere and maintained thereat for 10-15 hours. Here, if the conditions such as air atmosphere, temperature, and time are not satisfied the desired tube-shaped rod cannot be obtained. Therefore, it is preferred that the above conditions be met.

Figure 8:
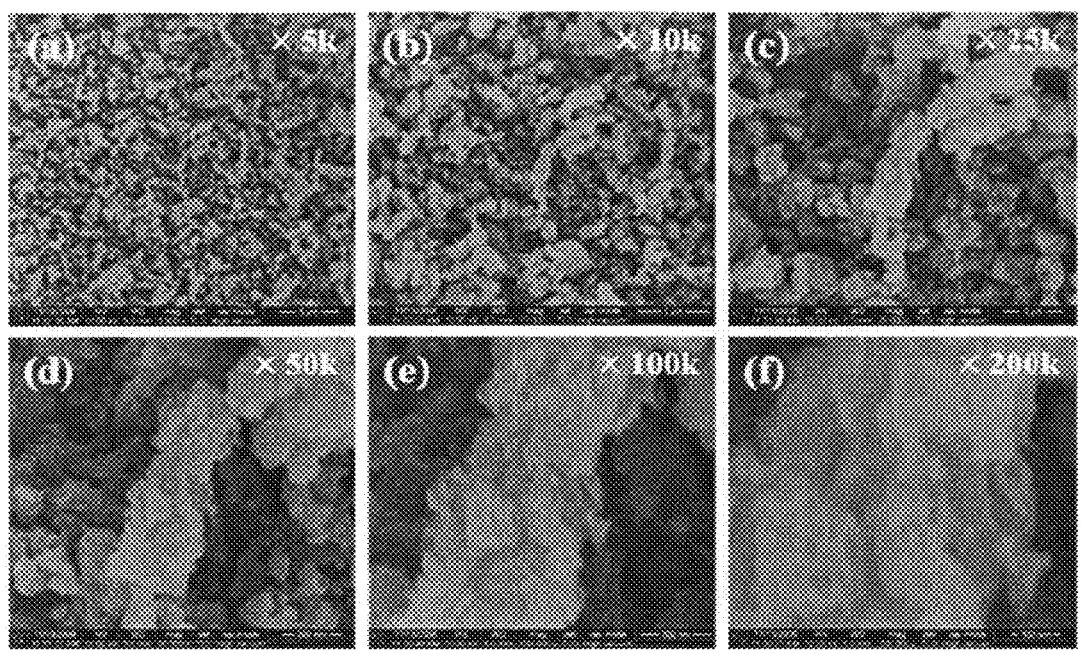
FIG. 8 shows the pictures of *Bacillus* bacteria/transition metal oxides organic-inorganic composite manufactured according to the present invention after calcination at 300° C. taken under Field Emission Scanning Electron Microscopy (FESEM)

The shape of the final powder obtained as a result of the calcinations can be observed via FESEM pictures. Its diameter was shown to have been decreased by 100-300 nm as compared to that of the organic-inorganic composite after vacuum dry (FIG. 8).

Figure 9:
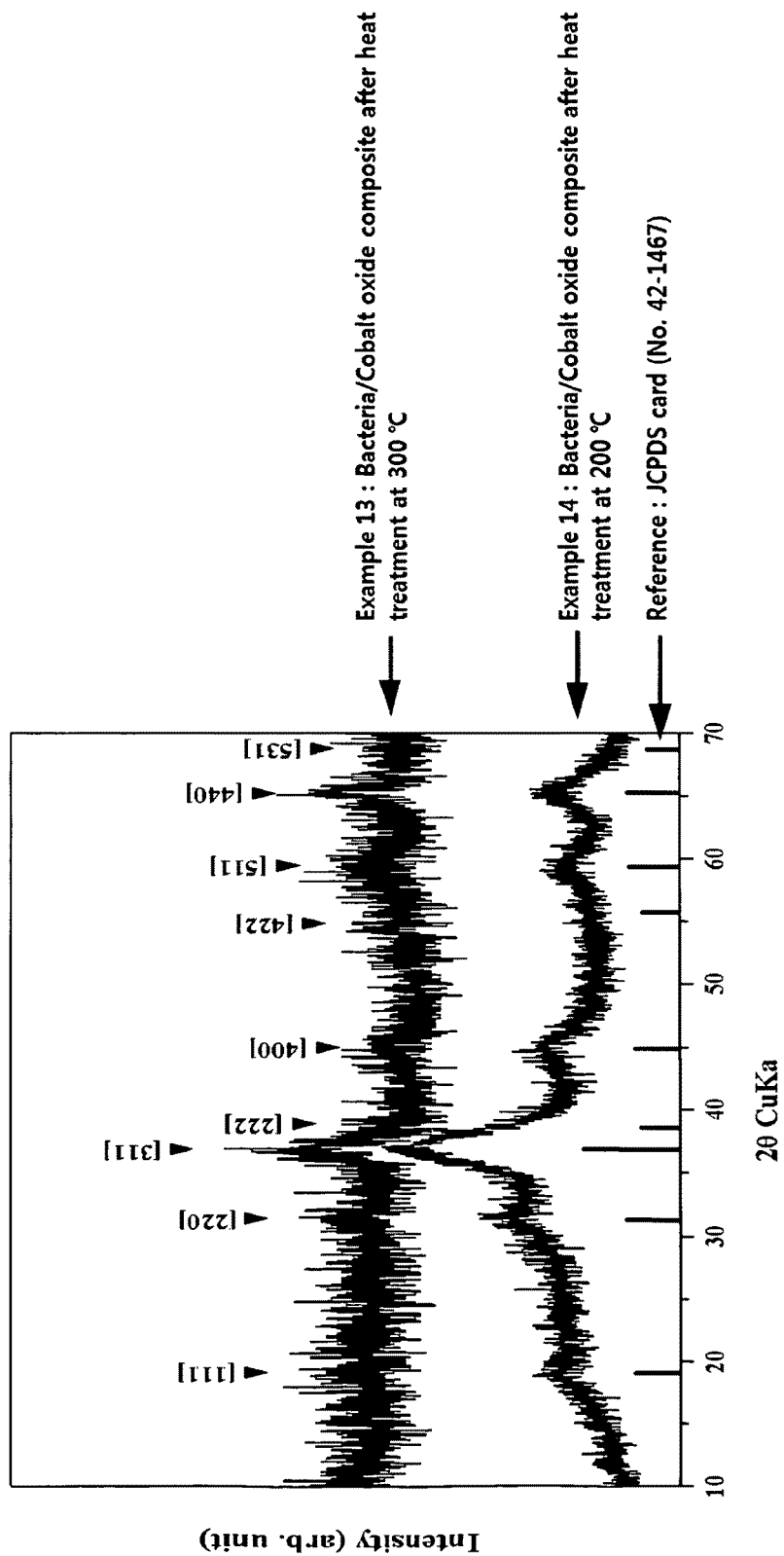
FIG. 9 shows an x-ray diffraction pattern (XRD) of *Bacillus* bacteria/cobalt oxide, an embodiment of *Bacillus* bacteria/transition metal oxides organic-inorganic composite of the present invention, after calcination at 200° C. and 300° C., respectively.

The kind of phase and crystalline structure of thus obtained product after calcinations can be confirmed by X-ray Diffraction patterns (XRD) (FIG. 9). According to FIG. 9, the powder obtained as a result of calcinations shows the same XRD as that of $Co_3O_4$ (JCPDS card No. 42-1467).

The bacteria/transition metal oxides organic-inorganic composite and tube-shaped transition metal oxides rod can be used in electrochemical elements, more particularly, lithium ion secondary batteries, electric double layer super capacitor, etc.

Therefore, in the present invention, in order to determine the applicability of the above organic-inorganic composite and tube-shaped rod nanopowder as an anode active material of lithium second batteries, an electrode for lithium battery was manufactured separately and by using a half battery the electrochemical properties was evaluated. In the above lithium ion secondary battery, the increase in electric charge of lithium, which can react per each unit molecular weight of anode active material to be used, and the increase in limitation against particle aggregation during charge/discharge, results in increase in electrochemical properties.

First, the above manufactured organic-inorganic composite, tube-shaped rod powder obtained after calcinations, a conductive additive and a binder were dissolved in an inert organic solvent and then mixed uniformly by sonication and vortexing. Then, the above mixture in the state of slurry is coated thinly onto the copper current collector to prepare an electrode.

The half battery is prepared in such a manner that lithium metal is used as a negative electrode, the above-mentioned organic-inorganic composite and tube-shaped rod powder obtained after calcination is used as a positive electrode, wherein electrolyte and a separator are added in between the two electrodes. Thus prepared battery was evaluated of charge/discharge cycle by changing the current density being flowed in within the area of 0.01-3.0 V.

Of the above manufactured organic-inorganic composite and tube-shaped rod powder obtained after calcination, *Bacillus* bacteria/cobalt oxide and the powder obtained after calcination at 300° C. were measured of their electrochemical properties. Further, pure *Bacillus* bacteria, commercially available $Co_3O_4$ and pure cobalt oxide which was synthesized under the same synthetic condition as in Example 10 of the present invention except that *Bacillus* bacterial template was not used, all used as control, were measured of their electrochemical properties.

Figure 10:
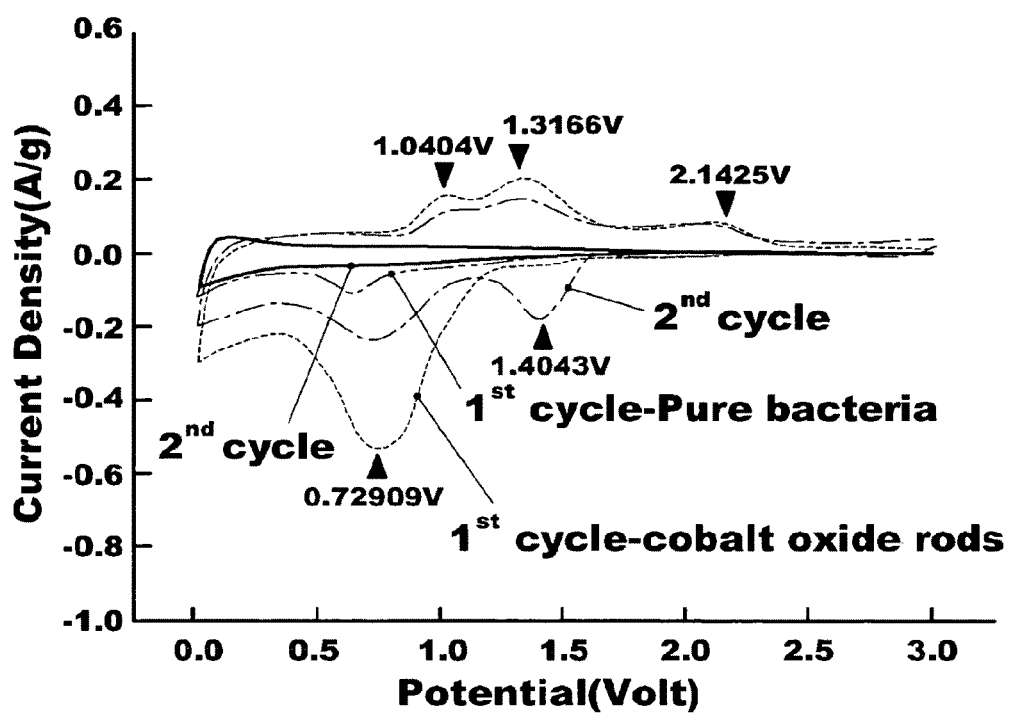
FIG. 10 shows a graph of curves representing the change in current according to change in voltage obtained by measurement of electrochemical properties of *Bacillus* bacteria/cobalt oxide organic-inorganic composite and organic bacteria of the present invention.
Figure 11:
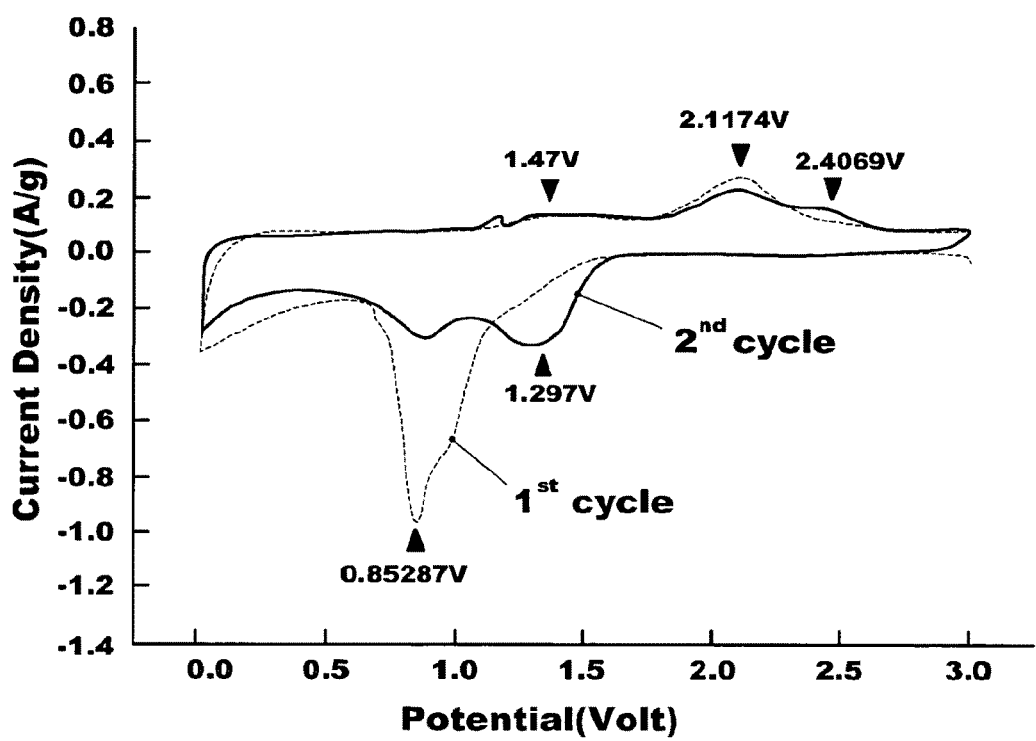
FIG. 11 shows a graph of curves representing the change in current according to change in voltage obtained by measurement of electrochemical properties of *Bacillus* bacteria/cobalt oxide organic-inorganic composite after calcination at 300° C.

The measurement of the properties of the electrodes manufactured according to the method mentioned above revealed that both the organic-inorganic composite of the present invention and tube-shaped rod powder obtained after calcination had higher output properties capable of high capacity than those of control. In fact, they maintained the high capacity during the test of 100 cycles thus showing excellent stability (FIGS. 10 and 11)

The present invention is described further in detail with reference to the following examples, however, they should not be construed as limiting the scope of the present invention.

EXAMPLES

Examples 1-3

5 μL of *Bacillus* bacteria stock solution, which was kept frozen, was collected, inoculated to a test tube containing 5 mL LB broth and then cultured in a revolving incubator at 37° C. at 200 rpm. After culturing for 10-12 hours, 500 μL each of the culture was collected and subcultured in 5 different Erlenmeyer flasks containing 200 mL of liquid culture medium. After subculturing for 5 hours, the bacterial culture was centrifuged at 12,000 rpm for 20 min to divide it into bacterial cluster and supernatant. The resulting supernatant and the bacteria cluster in the bottom portion were washed twice with deionized water and then centrifuged. Then, the bacterial concentration was adjusted to 1.0 ($=1 \times 10^8$ cells/mL) at 600 nm using UV spectrophotometer while adding 1 L or more of deionized water. While stirring the above dispersed bacterial suspension, the molarity of $CoCl_2 \cdot 6H_2O$, one of the chloride metal substances used in the present invention, was weighed to prepare 1, 10, 100 mM, respectively, and dissolved in 100, 100, 200 mL, respectively, and then stirred at room temperature for more than 1 hour. Then, the above solution was slowly added at a rate of about 1 mL/min to the solution which was kept stirring and contained bacterial suspension. The above mixture was stirred at room temperature for more than 1 hour for the uniform dispersion of cobalt precursor and bacteria. Then, the molarity of $NaBH_4$, which was used as a reducing agent, was adjusted to prepare 5, 10, 500 mM solutions, respectively, by dissolving them in 100 mL of deionized water, and stirred them at room temperature for 30 min. 100, 50, 12 mL each of thus prepared 5, 10, 500 mM $NaBH_4$ solutions, respectively, was slowly added into the mixture containing cobalt precursor and bacteria, and then kept for 1 hour at room temperature. Then, the resultant was refluxed at 25° C. for 12 hours and centrifuged at 10,000 rpm for 20 min to divide it into a supernatant and a precipitate. The supernatant was removed and the precipitate on the bottom portion was washed 3-4 times with deionized water and acetone. Here, the deposited precipitate is in such a state that transition metal oxides are evenly distributed and attached to the *Bacillus* bacterial surface. The deposit in pink, light green and black colors depending on the synthetic conditions were dried under vacuum at 60° C. under $10^{-2}$ torr for 6 hours and finally obtained the *Bacillus* bacteria/cobalt oxide organic-inorganic composite.

In case of the black final deposit obtained in Example 3, due to the concentration of the reducing agent, $NaBH_4$, cobalt metal not cobalt oxide was excessively refluxed and the rod-shape was hard to maintain.

Examples 4-7

*Bacillus* bacteria/cobalt oxide organic-inorganic composite was obtained by using the same synthetic method as in Examples 1-3, except that the concentrations of bacteria, cobalt chloride precursor/$NaBH_4$ reducing agent were fixed at 1.5 mM and 10 mM, respectively, the amount of cobalt chloride precursor was fixed at 100 mL, as shown in the following Table 1, while observing the change in acidity according to the change in the amount of $NaBH_4$ being added. Further, the respective color of the organic-inorganic composite relative to each deposit is shown in the following Table 1.

Example 8

*Bacillus* bacteria/cobalt oxide organic-inorganic composite was obtained by using the same synthetic method as in Examples 4-7, except that bacterial concentration was fixed at 2.0 as shown in the following Table 1 and acidity was adjusted to 8.0 by adding 20 mL of $NaBH_4$.

Examples 9-11

The synthetic method same as in Examples 1-8 was used. Because the amount of the final deposit was not much in previous Examples, *Bacillus* bacteria/cobalt oxide organic-inorganic composite was manufactured by increasing the concentrations of bacteria, cobalt chloride precursor/$NaBH_4$ reducing agent to 2.0 mM and 50 mM, respectively, fixing the amount of cobalt chloride precursor at 400 mL, as shown in the following Table 1, while changing the amount of $NaBH_4$ being added. The colors of the organic-inorganic composite of the final deposit are shown in the following Table 1.

Example 12

The synthetic method same as in Example 10 was used except that a metal chloride precursor shown in the following Table 1 was used. Further, the colors of *Bacillus* bacteria/iron oxide organic-inorganic composite, the final deposited precipitate is shown in the following Table 1.

Examples 13-15

The synthetic method same as in Example 10 was used except that, after drying under vacuum of the final deposited precipitate, calcination was performed for the manufacture of tube-shaped product as in Example 1 according to the respective temperature and air atmosphere shown in the following Table 2. More specifically, the calcination was performed to manufacture the tube-shaped rod in such a manner that the temperature was increased at the rate of 5° C./min until it reached 150° C., 200° C., 300° C., respectively, and then maintained thereat for 12 hours, respectively. Here, the deposit in emerald color formed as a result of the synthesis was calcined at the respective temperature and exhibited the colors shown in the following Table 2.

TABLE 1

| | Bacteria used Bacillus Conc. (O.D. 600 nm) | Metal Precursor used type Co | Fe | Conc. (mM) | Amount added (mL) | pH | Synthesis Temp. | Color |
|---|---|---|---|---|---|---|---|---|
| Ex. 1 | 1.0 | $CoCl_2 \cdot 6H_2O$ | — | 1/5 | 100/100 | 7.02 | 25° C. | Light Pink |
| Ex. 2 | | | | 10/10 | 100/50 | 7.63 | | Light Green |
| Ex. 3 | | | | 100/500 | 200/12 | 8.10 | | Black |
| Ex. 4 | 1.5 | | | 10/10 | 100/2 | 8.20 | | Light Pink |
| Ex. 5 | | | | | 100/5 | 8.03 | | Light Pink |
| Ex. 6 | | | | | 100/10 | 8.00 | | Pink |
| Ex. 7 | | | | | 100/30 | 2.61 | | Pink |
| Ex. 8 | 2.0 | | | 10/10 | 100/20 | | | Pink |
| Ex. 9 | 2.0 | | | 50/50 | 400/92 | | | Light Purple |
| Ex. 10 | | | | | 400/200 | | | Emerald |
| Ex. 11 | | | | | 400/300 | | | Brown |
| Ex. 12 | 2.0 | — | $FeCl_3$ | 50/50 | 400/200 | | 25° C. | Ocher |

TABLE 2

| Organic/ Inorganic composite | Bacteria used Bacillus Conc. (O.D. 600 nm) | Metal precursor/ reducing agent used $CoCl_2 \cdot 6H_2O$/ $NaBH_4$ Conc. (mM) | Amount added (mL) | Synthesis Temp. | Calcination Temp. | Color Before Synthesis | After Synthesis |
|---|---|---|---|---|---|---|---|
| Ex. 13 | Bacillus/ $Co_3O_4$ | 2.0 | 50/50 | 400/200 | 25° C. | 300° C. | Emerald | Black |
| Ex. 14 | | | | | | 200° C. | | Dark Brown |
| Ex. 15 | Bacillus/ $Co_3O_x$ | | | | | 150° C. | | Emerald |

Comparative Examples 1-3

In order to compare and analyze the characteristics of the second batteries manufactured by using the organic-inorganic composite of one dimension consisting of zero dimension and tube-shaped rod prepared in the above Examples 10 and 14, powder was obtained from pure Bacillus bacterial culture by drying it under vacuum and commercially available $Co_3O_4$ powder and pure cobalt metal oxide nanopowder, all the above powders being used as control. The difference between the pure cobalt oxide of the Comparative Example 1 and the Example 10 is that the synthesis is conducted without using Bacillus bacteria as template. The other synthetic methods are same as that in Example 10. The colors of the final deposit and the powders used are shown in the following Table 3.

TABLE 3

| | Bacteria used Bacillus Conc. (O.D. 600 nm) | Metal precursor used type Co | Fe | Metal precursor/ reducing agent used $CoCl_2 \cdot 6H_2O$/ $NaBH_4$ Conc. (mM) | Amount added (mL) | Synthesis Temp. | Color |
|---|---|---|---|---|---|---|---|
| Comp. Ex. 1 | — | $CoCl_2 \cdot 6H_2O$ | — | 50/50 | 400/200 | 25° C. | Black |
| Comp. Ex. 2 | | Pure bacteria | | | | | Ivory |
| Comp. Ex. 3 | | Commercially available $Co_3O_4$ | | | | | Ultramarine |

Test Example 1

In order to compare and evaluate the organic-inorganic composite prepared in Example 10, tube-shaped rod anode active material prepared in Example 13, pure *Bacillus* bacteria powder prepared in Examples 1-3, and commercially available $Co_3O_4$ powder as anode active material for secondary batteries electrodes were manufactured and then the capacity of half batteries were measured.

(a) Manufacture of Electrodes

The electrode comprises an anode active material, either the organic-inorganic composite rod prepared in Example 10 or the tube-shaped rod prepared in Example 13, used in the amount of 0.5-1 mg; Kynar 2801(PVdF-HFP), which is used as a binder; and a conductive agent (MMM Carbon). The above three components were weighed so that the weight ratio became 60:20:20, and then dissolved in N-methyl-pyrrolidone (NMP), an inert organic solvent, to obtain it in a slurry form. Then, the above slurry was coated on the copper foil serving as a collector, dried in an oven for 4 hours to evaporate the organic solvent and then punched by pressing to obtain a circle with a diameter of 1 cm.

As control, pure cobalt metal oxide nanopowder prepared in the above Comparative Example 1, pure *Bacillus* bacteria powder, commercially available $Co_3O_4$ powder prepared in the above Comparative Examples 2-3, which are served as anode active material and Kynar 2801, which is a binder for a conductive agent (MMM Carbon), were weighed so that the weight ratio became 60:20:20, and then dissolved in an inert organic solvent, to obtain it in a slurry form. Then, the subsequent process was done the same as in the manufacture of electrodes suggested in the sample of the above Example 10 and Example 13.

(b) Manufacture of a Half Battery for Evaluation of Electrochemical Properties and the Measurement In order to study the electrochemical properties of the organic-inorganic composite and tube-shaped rod introduced in the present invention, a half battery of Swagelok type was prepared in such a manner that lithium using metal ions as a negative electrode, using the electrode of the above organic-inorganic composite and tube-shaped rod manufactured in (a) or the powder manufactured in Comparative Examples 1-3 as a positive electrode, inserting a separation membrane (Celgard 2400) and electrolytes in between the two electrodes. The electrolytes used were a mixture comprising ethylene carbonate (EC) and dimethyl carbonate (DMC) in a volume ratio of 1:1 wherein $LiPF_6$ was dissolved. The entire process of manufacturing the above half battery was conducted in a Glove box which was filled with argon gas, an inert gas. The above Swagelok type half-cells were measured by changing voltage in the range of 0.01-3.0 V at 0.01 mV/sec in potentiostatic mode by using charge/discharge cycler (WBCS 3000, WonA Tech., Korea) and by changing current density in galvanostatic mode. The graph showing the change in voltage according to the time or capacity measured was analyzed and the electrochemical properties were evaluated. Here, the current density was reversely converted from the theoretical capacity of $Co_3O_4$, one of the cobalt oxides, and was C/10, and C/5, respectively, and a total of 100 cycles of charge/discharge test were performed at each current density.

The cyclic voltamogram (CV) graphs by the measurement according to the potentiostatic mode are well shown in FIG. 10 and FIG. 11. FIG. 10 shows the results of measurement of anode active material consisting of pure *Bacillus* bacteria and the *Bacillus* bacteria/cobalt oxide organic-inorganic composite suggested in the present invention. According to the results, pure *Bacillus* bacteria hardly reacted with lithium in the measurement of lithium second batteries.

Figure 12:
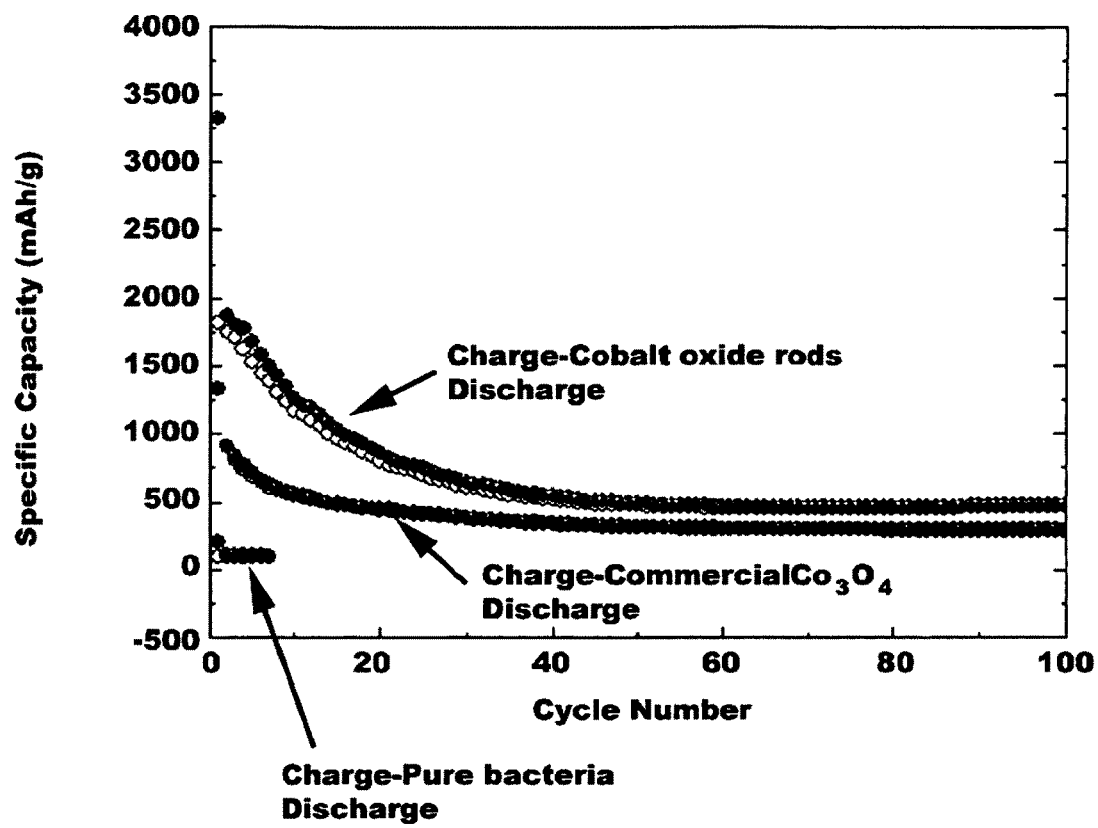
FIG. 12 shows a result of comparison between the curve representing the capacity change until the 100 cycles of test for *Bacillus* bacteria/cobalt oxide organic-inorganic composite manufactured according to the present invention and the curve representing the capacity change of a commercially available cobalt oxide and organic bacteria.
Figure 13:
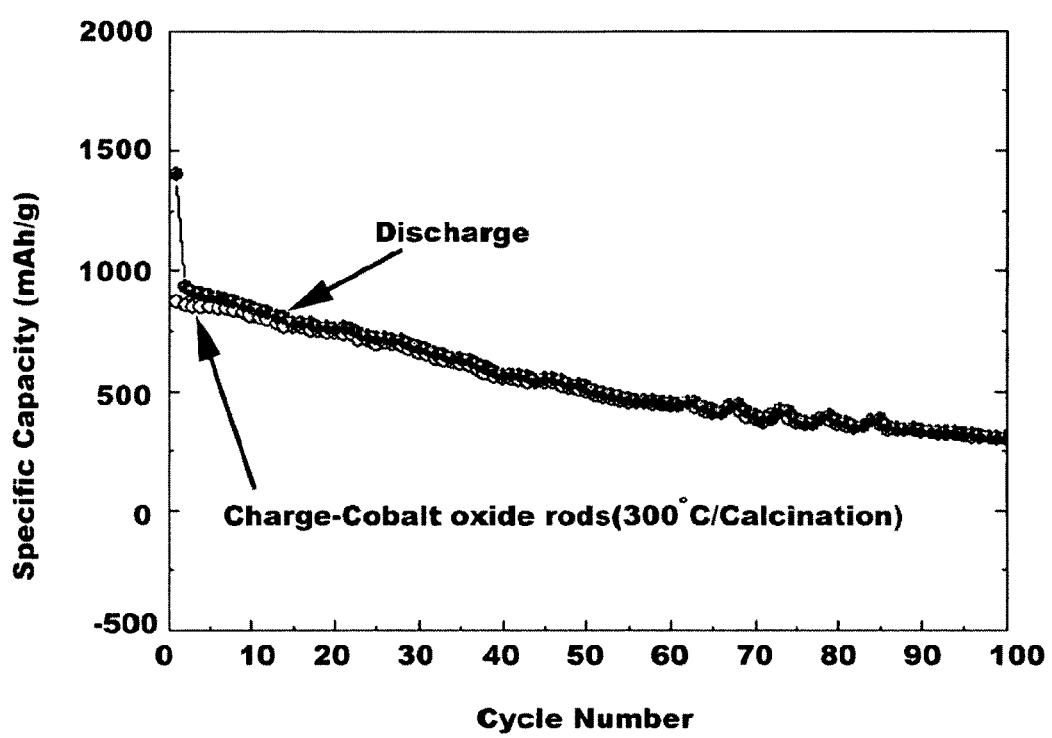
FIG. 13 shows a curve representing the capacity change until the 100 cycles of test for *Bacillus* bacteria/cobalt oxide organic-inorganic composite after calcination at 300° C.

Further, FIG. 12 and FIG. 13 show the result of conducting 100 cycles of charge/discharge test for anode active materials of Examples 10 and 13 and Comparative Examples 2 and 3 while supplying C/5 current density.

From the above comparison, it was confirmed that the anode active materials manufactured by using the organic-inorganic composite of the present invention and the tube-shaped rod exhibit higher capacity and superior long term cycle retention than those of the pure *Bacillus* bacteria or commercially available $Co_3O_4$.

The following Table 4 and Table 5 show the discharge capacity at the time of performing 100 cycles of charge/discharge test for the organic-inorganic composite manufactured in Example 10, tube-shaped rod manufactured in Example 13 and pure cobalt metal oxide nanopowder manufactured in Comparative Examples 1-3, pure *Bacillus* bacteria powder and commercially available $Co_3O_4$, in the course of evaluating their secondary batteries, while supplying C/5 and C/10 current density.

TABLE 4

| | Active Material | Discharge Capacity(mAh/g) C/5 | | | | |
|---|---|---|---|---|---|---|
| | | 10 cycle | 30 | 50 | 80 | 100 |
| Ex. 10 | Bacteria/Cobalt oxide organic•inorganic composite | 1261 | 647 | 491 | 461 | 477 |
| Ex. 13 | Bacteria/Cobalt oxide organic•inorganic composite - after calcination at 300° C. | 847 | 688 | 515 | 372 | 303 |
| Comp. Ex. 2 | Pure *Bacillus* Bacteria | 99 | | | | |
| Comp. Ex. 3 | Commercially available $Co_3O_4$ | 546 | 379 | 313 | 292 | 283 |

TABLE 5

| | Active Material | Discharge Capacity (mAh/g) C/10 | | | | |
|---|---|---|---|---|---|---|
| | | 10 cycle | 30 | 50 | 80 | 100 |
| Ex. 10 | Bacteria/Cobalt oxide organic•inorganic composite | 1439 | 760 | 542 | 435 | 391 |
| Comp. Ex. 1 | Pure cobalt oxide | 557 | 206 | 148 | 101 | 80 |

The above Table 4 and Table 5 show that the organic-inorganic composite manufactured in Example 10 of the present invention, the tube-shaped rod manufactured in Example 13, both as anode active materials, have superior high capacity and enable to maintain it during a long term cycle than those of pure cobalt oxide nanopowder or pure *Bacillus* bacteria powder manufactured in Comparative Examples 2-3, and commercially available $Co_3O_4$ powder.

From the above, it is apparent that the organic-inorganic composite and tube-shaped rod material of one dimension consisting of zero dimensional transition metal oxides nanopowder can not only attain high capacity from the zero dimensional nanopowder, but also maintain the high capacity during a test with a high number of cycles at the time of reaction with lithium due to little change in volume.

INDUSTRIAL APPLICABILITY

The present invention resolved the drawbacks of the conventional anode active material used for the lithium secondary batteries causing a large change in volume in the reaction with lithium and low capacity thus reducing the capacity according to the cycle number by using bacteria as a template, and manufacturing an organic-inorganic composite rod of one dimension consisting of zero dimension which is manufactured by binding between high capacity nano metal oxides with bacterial surface.

In particular, the method of the present invention to manufacture the above organic-inorganic composite, wherein a transition metal precursor having the cationic properties are directly attached to the bacterial surface based on the fact that bacterial surface is negatively charged, and then refluxing the resultant with transition metal oxides, which is simple and cost-effective enabling synthesis in various forms depending on the bacteria being used. Further, because bacteria, which can be produced at low temperature and served as a template, can be produced massively thus it is expected that the method of the present invention can be applied to various fields of industry including lithium secondary batteries, and electric double layer super capacitor.

As describe above, while the present invention has been disclosed for the purpose of illustration with reference to the aforementioned preferred embodiment, more various appliances can be connected to a living network according to the present invention, and it will be understood by those skilled in the art that the foregoing embodiment can be improved, modified, substituted or added in a variety of ways without departing from the technical spirit and scope of the invention as defined by the appended claims.

The invention claimed is:

1. A method of manufacturing a transition metal oxide rod;
    wherein an organic/inorganic composite comprising bacteria and a transition metal oxide is calcined to form a tube-shaped rod under air atmosphere; and
    wherein the surface of said bacteria is attached with transition metal oxide by a redox reaction between the negative charge on the surface of said bacteria and the positive charge on said transition metal ions.

2. The method of manufacturing a transition metal oxide rod according to claim 1;
    wherein the calcination is performed in such a manner that the temperature is increased at a rate of 1-10° C./min until it reaches 300° C. and then maintained thereat for 10-15 hours.

3. A tube-shaped transition metal oxide rod manufactured by the method of claim 1.

4. An anode active material for secondary battery comprising the rod of claim 3.

5. A secondary battery comprising said anode active material of claim 4.

6. A tube-shaped transition metal oxide rod manufactured by the method of claim 2.

7. A method of manufacturing a transition metal oxide rod according to claim 2,
    wherein said bacteria and said transition metal oxide are refluxed in the presence of $NaBH_4$.

* * * * *